US009831060B2

(12) United States Patent
Kawase

(10) Patent No.: US 9,831,060 B2
(45) Date of Patent: Nov. 28, 2017

(54) X-RAY GENERATING APPARATUS AND RADIOGRAPHY SYSTEM USING THE SAME

(71) Applicant: CANON KABUSHIKI KAISHA, Tokyo (JP)

(72) Inventor: Junya Kawase, Yokohama (JP)

(73) Assignee: Canon Kabushiki Kaisha, Tokyo (JP)

(*) Notice: Subject to any disclaimer, the term of this patent is extended or adjusted under 35 U.S.C. 154(b) by 0 days.

(21) Appl. No.: 15/644,003

(22) Filed: Jul. 7, 2017

(65) Prior Publication Data

US 2017/0316911 A1 Nov. 2, 2017

Related U.S. Application Data

(63) Continuation of application No. 14/882,607, filed on Oct. 14, 2015, now Pat. No. 9,741,524.

(30) Foreign Application Priority Data

Nov. 12, 2014 (JP) ................................ 2014-229592

(51) Int. Cl.
*A61B 6/00* (2006.01)
*H01J 35/00* (2006.01)
*H01J 35/18* (2006.01)

(52) U.S. Cl.
CPC ......... *H01J 35/18* (2013.01); *H01J 2235/087* (2013.01); *H01J 2235/186* (2013.01)

(58) Field of Classification Search
CPC . H01J 2235/087; H01J 2235/186; H01J 35/18
See application file for complete search history.

(56) References Cited

U.S. PATENT DOCUMENTS

2015/0279608 A1* 10/2015 Miyaoka ................ H01J 37/16 378/138

FOREIGN PATENT DOCUMENTS

JP 2009-43658 A 2/2009

* cited by examiner

*Primary Examiner* — Dani Fox
(74) *Attorney, Agent, or Firm* — Fitzpatrick, Cella, Harper & Scinto

(57) ABSTRACT

Heat dissipation of a target is enhanced in a transmissive X-ray generating apparatus where an anode member constitutes a part of a container. An anode member configured to hold a target is divided into an outer anode member, which is configured to hold the target and is connected to a container, and an inner anode member, which is joined to an insulating tube and is closer to an electron emitting portion than the outer anode member is. The outer circumferential surface of the inner anode member is joined to the outer anode member via a joining member. Heat generated by the electron emitting portion is dissipated mainly from the inner anode member via the insulating tube, or directly, to an insulating liquid.

19 Claims, 3 Drawing Sheets

X-RAY GENERATING APPARATUS AND RADIOGRAPHY SYSTEM USING THE SAME

The present application is a continuation of U.S. application Ser. No. 14/882,607, filed on Oct. 14, 2015, the entire disclosure of which is incorporated by reference herein.

BACKGROUND OF THE INVENTION

Field of the Invention

The present invention relates to an X-ray generating apparatus applicable to, for example, medical equipment and non-destructive testing apparatus, and to a radiography system using the same.

Description of the Related Art

X-ray generating apparatus in general have a built-in X-ray generating tube as an X-ray source. The X-ray generating tube includes a vacuum container in which a cathode is mounted to one opening of an insulating tube and an anode is mounted to the other opening of the insulating tube. An electron emitting source is connected to the cathode, and the anode includes a target. The X-ray generating tube generates an X-ray by applying high voltage between the cathode and the anode, and irradiating the target with an electron beam that is emitted from the electron emitting source as a result of the voltage application.

As an example of the X-ray generating apparatus, in Japanese Patent Application Laid-Open No. 2009-43658, there is disclosed a structure in which the anode is fixed to a metal casing, which is a container of the X-ray generating apparatus, in a manner that makes an output opening of the metal casing and an output window of the X-ray generating tube concentric with each other. With the structure of Japanese Patent Application Laid-Open No. 2009-43658, an X-ray emitted from the output window is radiated to the outside of the X-ray generating apparatus. This structure is connected thermally and electrically from the target in the X-ray generating tube to an anode member, which holds the target, and further to the metal casing of the X-ray generating apparatus, thereby dissipating heat of the target, which has risen in temperature when irradiated with an electron beam.

In the X-ray generating apparatus structured as disclosed in Japanese Patent Application Laid-Open No. 2009-43658, other electronic energies than an X-ray that are generated from a collision between electrons and the target for X-ray irradiation are converted into heat, which is dissipated from the target via the anode member to the metal casing. On the other hand, an electron emitting portion of the electron emitting source that emits the electrons generates heat as well, and a part of the generated heat is dissipated to a cathode member, which is opposed to the anode member relative to the vacuum container. The rest of the generated heat is released to the anode member, which is in proximity to the electron emitting portion, and is dissipated to the metal casing via the anode member. Accordingly, the generated heat from the target and a part of the generated heat from the electron emitting portion are conducted along a heat conduction path for heat dissipation from the anode member to the metal casing, and there is a fear that heat is not dissipated from the target satisfactorily.

High temperature in the target due to insufficient target heat dissipation has a fear of causing damage to the target such as the peeling, melting, or evaporation of a target layer, or a crack in a support substrate, which can result in fluctuations or a drop in X-ray output.

SUMMARY OF THE INVENTION

It is an object of the present invention to stabilize X-ray output in a transmissive X-ray generating apparatus in which an anode member constitutes a part of a container by enhancing the heat dissipation of a target. It is another object of the present invention to provide a highly reliable Radiography system by using this X-ray generating apparatus.

In order to achieve the above-mentioned object, according to a first embodiment of the present invention, there is provided an X-ray generating apparatus, including:

an X-ray generating tube including:

an anode including a transmissive target configured to generate an X-ray when irradiated with an electron beam, and an anode member configured to hold the transmissive target;

a cathode including an electron emitting source configured to irradiate the transmissive target with an electron beam, and a cathode member connected to the electron emitting source; and an insulating tube having a pair of ends in a tube axis direction, one end of which is connected to the anode member and the other end of which is connected to the cathode member; and a conductive container, which is connected to the anode member and is configured to house the X-ray generating tube, in which the anode member includes an outer anode member, which is configured to hold the transmissive target and is electrically connected to the conductive container, and an inner anode member, which is interposed between the outer anode member and the electron emitting source in the tube axial direction of the insulating tube and is joined to the insulating tube, and in which the inner anode member is connected to the outer anode member outside the insulating tube in a tube radial direction, in a manner that allows for heat transfer.

According to a second embodiment of the present invention, there is provided a radiography system, including: the X-ray generating apparatus of the first embodiment of the present invention; an X-ray detector configured to detect an X-ray that has been generated from the X-ray generating apparatus and transmitted through a subject; and a system control unit configured to control the X-ray generating apparatus and the X-ray detector in a coordinated manner.

Further features of the present invention will become apparent from the following description of exemplary embodiments with reference to the attached drawings.

BRIEF DESCRIPTION OF THE DRAWINGS

FIG. 3A and FIG. 3B are enlarged sectional views of FIG. 2 around the anode, in which FIG. 3A is an explanatory diagram of components and FIG. 3B is a diagram of heat conduction paths.

FIG. 4A and FIG. 4B are diagrams for schematically illustrating the structure around an anode of an X-ray generating apparatus according to another embodiment of the present invention in the form of enlarged schematic sectional views taken along the line 2-2 of FIG. 1, in which FIG. 4A is an explanatory diagram of components and FIG. 4B is a diagram of heat conduction paths.

DESCRIPTION OF THE EMBODIMENTS

Figure 1:
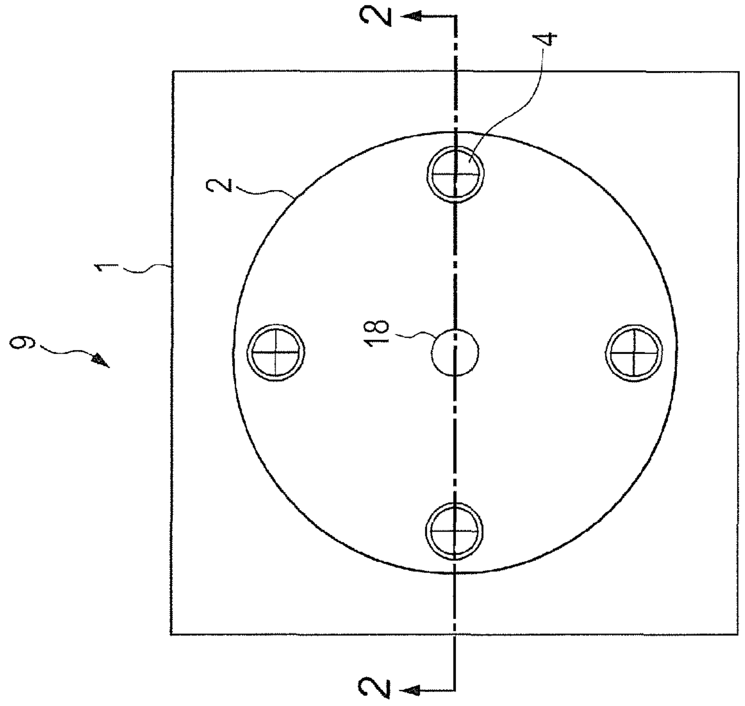
FIG. 1 is a schematic plan view of an X-ray generating apparatus according to an embodiment of the present invention, which is viewed from the outside of an anode.

Embodiments of the present invention are described below with reference to the drawings. However, the present invention is not limited to the embodiments. Known technologies in the technical field of the present invention are applied to parts that are not particularly described herein or illustrated in the drawings. In the present invention, "tube axial direction" and "tube radial direction" are the tube axial direction and tube radial direction of an insulating tube, which is described later.

Figure 2:
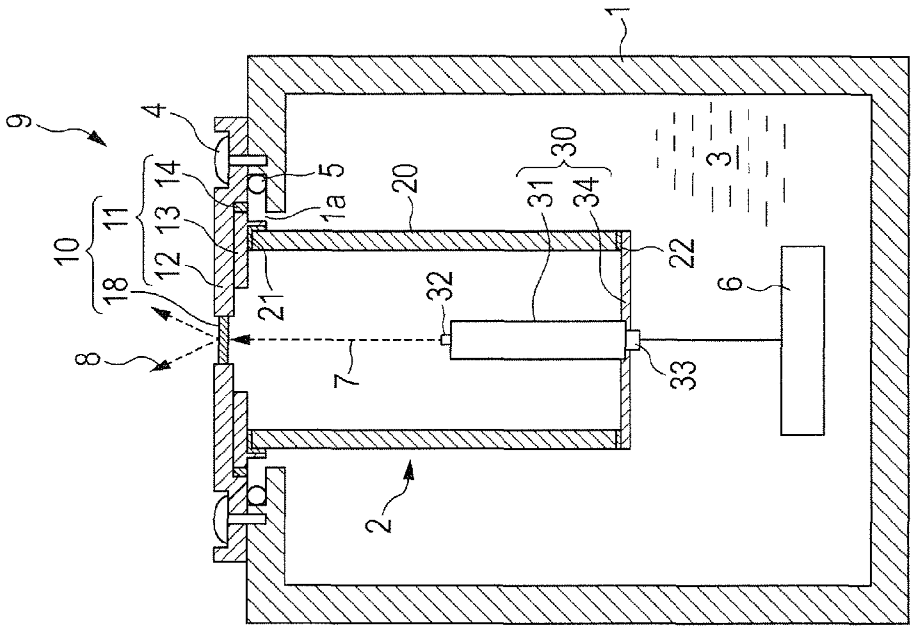
FIG. 2 is a diagram for schematically illustrating the structure of the X-ray generating apparatus according to the embodiment of the present invention, in the form of a schematic sectional view taken along the line 2-2 of FIG. 1.
Figure 3A:
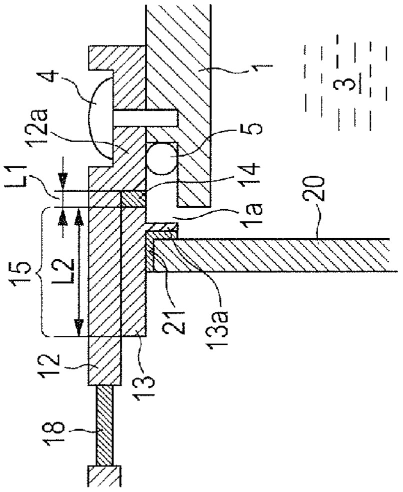

FIG. 1 is a view of an X-ray generating apparatus according to an embodiment of the present invention, which is viewed from outside of an anode. FIG. 2 is a schematic sectional view taken along the line 2-2 of FIG. 1. FIG. 3A is an enlarged sectional view of FIG. 2 around the anode. An X-ray generating apparatus 9 of the present invention includes a conductive container 1, which has an opening 1*a*, an X-ray generating tube 2, and a control portion 6 configured to drive the X-ray generating tube 2 with pulses. The internal space of the container 1 excluding the X-ray generating tube 2 and the control portion 6 is filled with an insulating liquid 3. The container 1 is, for example, a metal casing, to which the X-ray generating tube 2 is mounted around the opening 1*a* with the use of screws 4. The outer rim of the opening 1*a* of the container 1 is notched and recessed to create a space for sandwiching a sealing member 5 when the X-ray generating tube 2 is mounted. The opening diameter of the opening 1*a* formed in the container 1 is larger than the outer diameter of an insulating tube 20 of the X-ray generating tube 2, and the interior of the container 1 is hermetically sealed when the X-ray generating tube 2 is inserted to the opening 1*a* from the outside with the control portion 6 housed in the container 1 and the container 1 filled with the insulating liquid 3.

The X-ray generating tube 2 in the X-ray generating apparatus 9 of the present invention is a transmissive X-ray generating tube, which uses a transmissive target 18. The X-ray generating tube 2 includes the insulating tube 20, an anode 10 disposed at one end of the insulating tube 20 in the tube axial direction, and a cathode 30 disposed at the other end of the insulating tube 20. The insulating tube 20 is made from an insulating material such as a glass material or a ceramic.

The anode 10 includes the target 18 and an anode member 11 configured to hold the target 18. The anode member 11 in the present invention includes an inner anode member 13 and an outer anode member 12. The inner anode member 13 is hermetically joined to one end of the insulating tube 20 in the tube axial direction via a joining member 21. The outer anode member 12 holds the target 18 and is electrically connected to the container 1. In this example, as described above, the outer diameter of the outer anode member 12 is larger than the opening diameter of the opening 1*a* of the container 1, and the rim of the outer anode member 12 is hermetically mounted to the vicinity of the opening 1*a* of the container 1 with the screws 4.

Figure 3B:
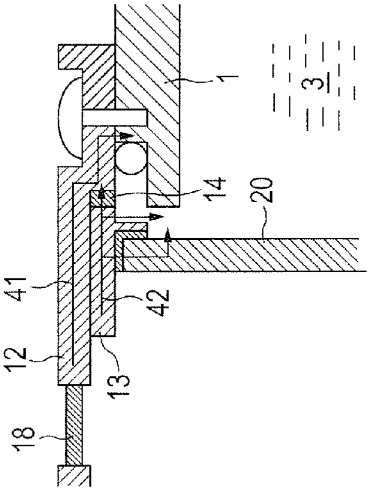

The inner anode member 13 in the present invention is interposed between the outer anode member 12 and an electron emitting source 31. On the outside of the insulating tube 20 in the tube radial direction, the inner anode member 13 is connected to the outer anode member 12 in a manner that allows for heat transfer. The heat transmissive connection between the inner anode member 13 and the outer anode member 12 in the present invention can be joining via a joining member or joining via a thermal fusion region. The joining member used is a material that is higher in heat conductivity than the inner anode member 13 and the outer anode member 12 both. The thermal fusion region can be formed by welding that is described later. The mode of joining illustrated in FIG. 2, FIG. 3A, and FIG. 3B is the one via a joining member 14. This heat transmissive connection portion stretches in a ring pattern about the tube axial direction, and can therefore be a hermetic joint. The connection portion may instead be discontinuous in the circumferential direction in the present invention. In the case where the connection portion is discontinuous, a separate measure is taken to hermetically join the inner anode member 13 and the outer anode member 12 to each other in a ring pattern with the use of a bonding material such as an inorganic adhesive, cement, or glass frit.

In the present invention, the inner anode member 13 and the outer anode member 12 are not joined via the joining member or the fusion region except for the heat transmissive connection portion, and are just in contact with each other on the surface. In FIG. 3A, a contact region 15 is illustrated, in which a surface of the inner anode member 13 and a surface of the outer anode member 12 are in contact with each other. In the contact region 15, minute gaps are dotted between the surface of the inner anode member 13 and the surface of the outer anode member 12, which causes the heat resistance to be higher between the inner anode member 13 and the outer anode member 12 than inside the inner anode member 13 or inside the outer anode member 12. In short, the gaps hinder the transfer of heat from one of the inner anode member 13 and the outer anode member 12 to the other.

In the present invention, heat generated in the target 18 is transmitted to the outer anode member 12 to which the target 18 is connected, and heat generated in an electron emitting portion 32 is dissipated to the inner anode member 13, which is closer to the electron emitting portion 32 than the outer anode member 12 is. Accordingly, the heat generated in the electron emitting portion 32 is not transmitted to the outer anode member 12.

Heat transfer from the inner anode member 13 to the outer anode member 12 in the tube axial direction of the insulating tube 20 is further suppressed in this example where the joining member 14, which joins the inner anode member 13 and the outer anode member 12, is disposed on the outer circumference of the inner anode member 13. In the connection portion where the inner anode member 13 and the outer anode member 12 are joined via the joining member 14, on the other hand, the heat resistance between the inner anode member 13 and the outer anode member 12 is lower than in the contact region 15 where the surfaces of the inner anode member 13 and the outer anode member 12 are in contact with each other, but the small connection areal dimensions in section hinder heat transfer from one of the inner anode member 13 and the outer anode member 12 to the other. Heat dissipated from the electron emitting portion 32 to the inner anode member 13 therefore is transmitted mainly to the insulating tube 20 and the insulating liquid 3, although partially transmitted to the outer anode member 12 via the joining member 14.

Heat conduction paths in the structure of FIG. 3A are illustrated in FIG. 3B. In FIG. 3B, a heat conduction path 41 leads from the target 18 to the container 1 via the outer anode member 12, and a heat conduction path 42 starts from the inner anode member 13. The inner anode member 13, which is closer to the electron emitting source 31 than the outer anode member 12 is, rises in temperature when heat generated in the electron emitting portion 32 reaches the inner anode member 13. This temperature rise, however, is not transmitted much to the outer anode member 12 through the contact region 15. Accordingly, a part of the temperature rise is transmitted to the outer anode member 12 via the joining member 14 and the rest is dissipated via the insulating tube 20, or directly, to the insulating liquid 3. Heat from the inner anode member 13 is therefore not transmitted to a part of the outer anode member 12 that is around the target 18, and heat generated in the target 18 is dissipated quickly to the container 1 via the outer anode member 12.

Placing the joining member 14 on the outer circumferential surface of the inner anode member 13 as illustrated in FIG. 3A is preferred in the present invention in terms of forming the heat conduction path 42 described above. In order to position the joining member 14 in this manner, it is preferred to form a tubular outer circumferential portion 12*a*, which protrudes toward the insulating tube 20, along the outer circumferential edge of the outer anode member 12 in the tube radial direction as illustrated in FIG. 3A and join the outer circumferential surface of the inner anode member 13 and the inner circumferential surface of the tubular outer circumferential portion 12*a*. Brazing filler metal such as silver brazing filler metal is preferred for the joining member 14.

A length L1 of the joining member 14 in the tube radial direction is set shorter than a length L2 of the contact region 15 to relieve the concentration of stress on the joining member 14, which is generated when a temperature rise in the target 18 causes the outer anode member 12 to expand in the tube radial direction. This is because the outer anode member 12 is structurally easy to bend in the tube axial direction.

The outer anode member 12 in the present invention is preferred to be a member that helps the dissipation of heat generated in the target 18 to the container 1. A material high in heat conductivity is accordingly preferred, for example, copper, tungsten, or copper tungsten. A material having a linear expansion coefficient close to that of the insulating tube 20 is preferred for the inner anode member 13, which is joined to the insulating tube 20. In the case where the insulating tube 20 is made from a ceramic, Kovar is preferred for the inner anode member 13.

Figure 4A:
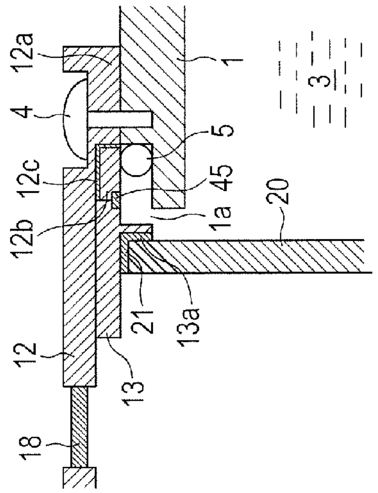

FIG. 4A is an example in which the inner anode member 13 and the outer anode member 12 are joined by welding, and a thermal fusion region 45 is illustrated in FIG. 4A. When the inner anode member 13 and the outer anode member 12 are joined by welding, the tubular outer circumferential portion 12*a*, which protrudes toward the insulating tube, is formed along the outer circumferential edge of the outer anode member 12 in the tube radial direction as in FIG. 3A, the outer circumferential surface of the inner anode member 13 and the inner circumferential surface of the tubular outer circumferential portion 12*a* are brought into contact with each other, and the contact surfaces are joined by welding. A preferred welding method is spot welding. Joining the inner anode member 13 and the outer anode member 12 via the thermal fusion region 45 by welding is a preferred mode because heat is transmitted continuously in the range of diffusion between metal members, which reduces heat resistance between the inner anode member 13 and the outer anode member 12.

If the same material as that of the inner anode member 13 is used for an inner circumferential region 12*b* of the tubular outer circumferential portion 12*a* which is joined to the inner anode member 13 by welding, welding is made easier even more. The joining region 12*b* in this case may be joined to adjacent regions by a joining member 12*c* such as brazing filler metal.

Figure 4B:
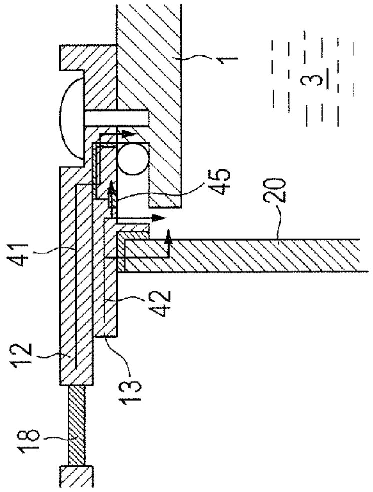

The heat conduction paths 41 and 42 are formed in the structure of FIG. 4A as illustrated in FIG. 4B. Heat generated in the target 18 is dissipated quickly to the container 1 via the outer anode member 12, without being affected by heat dissipation from the electron emitting portion 32.

As illustrated in FIG. 3A and FIG. 4A, a tubular outer circumferential portion 13*a*, which surrounds the outer circumferential surface of the insulating tube 20 and protrudes toward the cathode 30, may be formed in the inner anode member 13, which is joined to the insulating tube 20, to make a region where the inner anode member 13 is joined to the insulating tube 20 wider.

The cathode 30 according to the present invention includes the electron emitting source 31 and a cathode member 34, which is connected to the electron emitting source 31. The cathode 30 is hermetically joined to the other end of the insulating tube 20 via a joining member 22. Brazing filler metal such as silver brazing filler metal is preferred for the joining members 21 and 22. The cathode member 34 is, as is the inner anode member 13, formed unitarily with the insulating tube 20. Therefore, in the case where the insulating tube 20 is made from a ceramic, Kovar is preferred for the cathode member 34 as a metal material having a linear expansion coefficient close to that of a ceramic.

The target 18 is transmissive, and includes a transmissive substrate, which transmits an X-ray, and a target layer, which is formed on one surface on the inner side (cathode 30 side) of the transmissive substrate. The target layer contains a target metal, which emits an X-ray when irradiated with an electron beam. The target 18 is irradiated with an electron beam on the target layer, and emits an X-ray from a surface on the opposite side to the one surface of the transmissive substrate where the target layer is formed. The target layer contains as the target metal a metal element that is high in atomic number, melting point, and specific gravity. The target metal is selected from among metal elements of which the atomic numbers are equal to or more than 42. From the viewpoint of affinity to the transmissive substrate, it is more desirable to select from the group consisting of tantalum, molybdenum, and tungsten of which carbides have a negative standard free energy of formation. The target metal may be contained in the target layer as a single-component pure metal or an alloy composition pure metal, or as a metal compound such as a carbide, nitride, or oxynitride of the metal. Diamond or beryllium, for example, is preferred for the transmissive substrate. The target 18 is hermetically joined to the outer anode member 12 in a ring pattern via a joining member (not shown) that is made from silver brazing filler metal or the like.

The electron emitting source 31 is arranged so that the electron emitting portion 32 is opposed to the target 18. For example, a hot cathode such as a tungsten filament or an impregnated cathode, or a cold cathode such as a carbon nanotube can be used for the electron emitting source 31. The electron emitting source 31 may include a grid electrode (not shown) and an electrostatic lens electrode (not shown) for the purpose of controlling the beam diameter of an electron beam 7, the electron current density, on/off timing, and the like. A hot cathode is particularly favorable in the present invention. This is because, when a hot cathode is used as the electron emitting source 31, the electron emitting portion 32 keeps generating heat irrespective of whether the electron beam 7 is being emitted or not, which greatly affects how well heat is dissipated from the target 18 in an X-ray generating apparatus of the related art. In FIG. 2, a connection terminal 33 is illustrated.

As described above, the anode member 11 and the cathode member 34 are each hermetically joined to the insulating tube 20, thereby maintaining the vacuum sealing of the interior of the X-ray generating tube 2. When an appropriately set voltage is applied to the cathode 30 of the thus structured X-ray generating tube 2, the electron beam 7 is emitted from the electron emitting portion 32. The electron beam 7 collides with the target 18, and an X-ray 8 generated as a result is emitted to the outside of the container 1.

<Radiography System>

Figure 5:
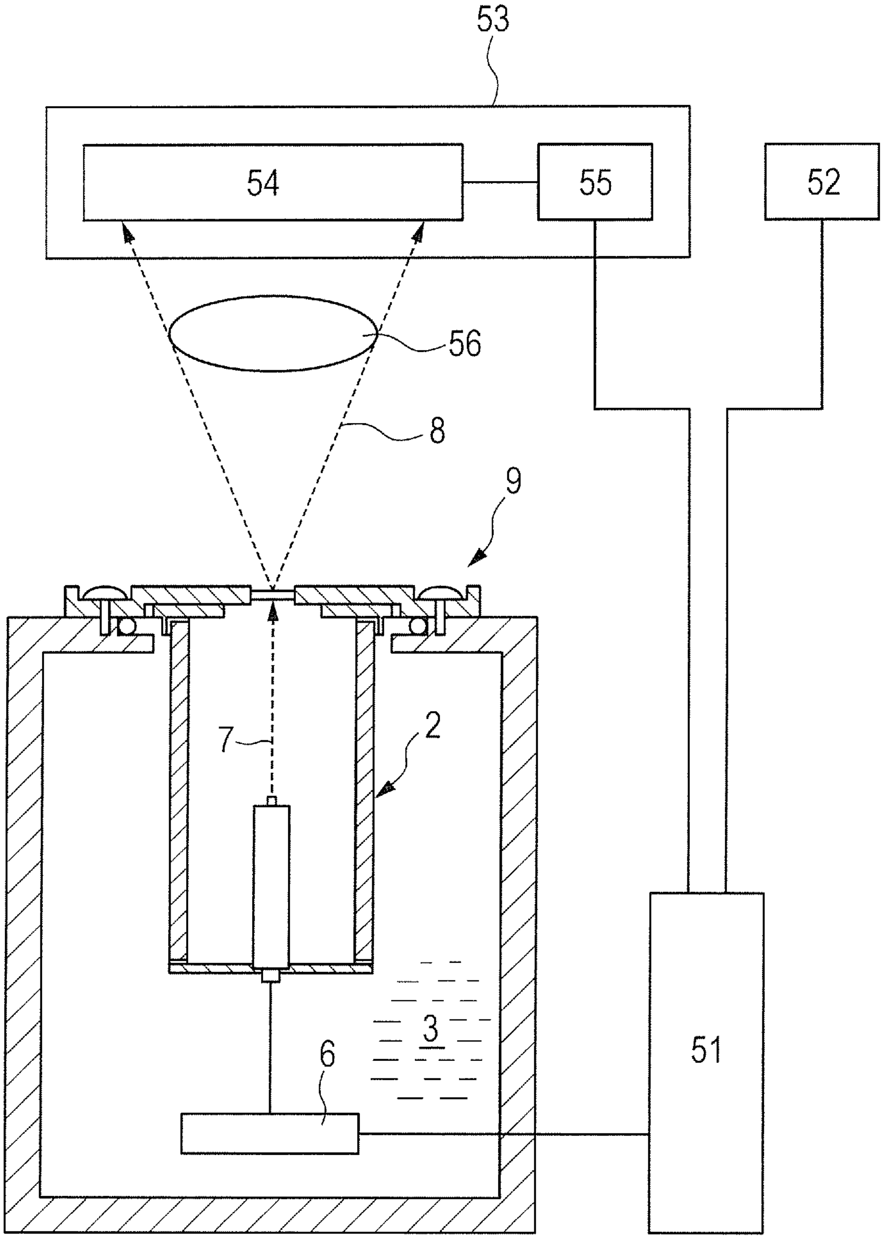
FIG. 5 is a diagram for schematically illustrating the structure of a radiography system according to the present invention.

A structural example of a radiography system, which includes the X-ray generating apparatus 9 of the present invention, is described next with reference to FIG. 5. The Radiography system of the present invention includes the X-ray generating apparatus 9 of FIG. 2, an X-ray detector 53, which detects the X-ray 8 generated by the X-ray generating apparatus 9 and transmitted through a subject to be examined 56 (hereinafter referred to as simply "subject"), and a system control unit 51. The system control unit 51 controls the X-ray generating apparatus 9 and the X-ray detector 53 in a coordinated manner. A control portion 6 outputs, under control of the system control unit 51, various control signals to the X-ray generating tube 2. The control signals output by the control portion 6 are used to control the emission state of the X-ray 8 emitted from the X-ray generating apparatus 9. The X-ray 8 emitted from the X-ray generating apparatus 9 is adjusted in irradiation range by a collimator unit (not shown) having a variable aperture, emitted to the outside of the X-ray generating apparatus 9, transmitted through the subject 56, and detected by an X-ray detector 54. The X-ray detector 54 converts the detected X-ray into image signals, which are output to a signal processing portion 55. The signal processing portion 55 performs, under control of the system control unit 51, given signal processing on the image signals, and outputs the processed image signals to the system control unit 51. Based on the processed image signals, the system control unit 51 outputs display signals for displaying an image on a display apparatus 52. The display apparatus 52 displays on a screen an image based on the display signals as a photographed image of the subject 56.

The Radiography system of the present invention is applicable to non-destructive testing of an industrial product, and the diagnosis of human and animal pathology.

According to the present invention, where the anode member is divided into the outer anode member and the inner anode member, heat is dissipated efficiently from the target to the outer anode member, thereby enhancing the heat dissipation of the target. An X-ray generating apparatus and a radiography system that are highly reliable are thus provided.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-229592, filed Nov. 12, 2014, which is hereby incorporated by reference herein in its entirety.

What is claimed is:

1. An X-ray generating apparatus comprising:

an X-ray generating tube comprising:

an anode comprising a transmissive target and an anode member connected to the transmissive target;

a cathode comprising an electron emitting source and a cathode member connected to the electron emitting source; and an insulating tube having a pair of ends in a tube axis direction, one end of which is connected to the anode member and the other end of which is connected to the cathode member; and a conductive container, which is connected to the anode member and is configured to house the X-ray generating tube and an electrically insulating liquid, wherein the anode member comprises an outer anode member configured to transfer a heat from the transmissive target to the conductive container, and an inner anode member configured to transfer a heat from the electron emitting source to the electrically insulating liquid.

2. The X-ray generating apparatus according to claim 1, wherein the inner anode member is configured to transfer the heat from the electron emitting source to the electrically insulating liquid via the insulating tube or directly.

3. The X-ray generating apparatus according to claim 1, wherein the inner anode member is joined to the outer anode member outside the insulating tube in a tube radial direction so as to form a joined portion between the inner anode member and the outer anode member.

4. The X-ray generating apparatus according to claim 3, wherein the inner anode member and the outer anode member contact each other so as to form a contact region inside from the joined portion in the tube radial direction.

5. The X-ray generating apparatus according to claim 3, wherein the inner anode member and the outer anode member do not join each other inside the joined portion in the tube radial direction.

6. The X-ray generating apparatus according to claim 1, wherein a heat transmissive connection portion, where the inner anode member is connected to the outer anode member in a manner that allows for heat transfer, stretches in a ring pattern about the tube axial direction.

7. The X-ray generating apparatus according to claim 1, wherein the inner anode member is connected to the outer anode member in a manner that allows for heat transfer by joining the inner anode member and the outer anode member via a joining member that is higher in heat conductivity than both of the inner anode member and the outer anode member.

8. The X-ray generating apparatus according to claim 7, wherein the outer anode member comprises a tubular outer circumferential portion protruding from an outer circumferential edge of the outer anode member in the tube radial direction toward the insulating tube, wherein an inner circumferential surface of the tubular outer circumferential portion and an outer circumferential surface of the inner anode member are joined to each other via the joining member, and wherein a surface of the inner anode member and a surface of the outer anode member are in contact with each other in the tube axial direction.

9. The X-ray generating apparatus according to claim 7, wherein, in the tube radial direction, a length of the joining member is shorter than a length of a region in which the inner anode member and the outer anode member are in contact with each other.

10. The X-ray generating apparatus according to claim 1, wherein the inner anode member is connected to the outer anode member in a manner that allows for heat transfer by joining the inner anode member and the outer anode member via a thermal fusion region.

11. The X-ray generating apparatus according to claim 10, wherein the outer anode member comprises a tubular outer circumferential portion protruding from an outer circumferential edge of the outer anode member in the tube radial direction toward the insulating tube, wherein an inner circumferential surface of the tubular outer circumferential portion and an outer circumferential surface of the inner anode member comprise contact surfaces at which the inner circumferential surface of the tubular outer circumferential portion and the outer circumferential surface of the inner anode member are in contact with each other, and a surface of the inner anode member and a surface of the outer anode member in the tube axial direction comprise contact surfaces at which the surface of the inner anode member and the surface of the outer anode member are in contact with each other, and wherein the inner circumferential surface of the tubular outer circumferential portion and the outer circumferential surface of the inner anode member are joined via the thermal fusion region on the contact surfaces.

12. The X-ray generating apparatus according to claim 10, wherein a region of the tubular outer circumferential portion, which is joined to the inner anode member via the thermal fusion region, is formed from the same material as the inner anode member.

13. The X-ray generating apparatus according to claim 1, wherein the outer anode member is positioned outside the conductive container in the tube axial direction.

14. The X-ray generating apparatus according to claim 1, wherein the inner anode member and the outer anode member are connected in a manner that allows for heat transfer on a side of a heat conduction path leading from the transmissive target to the conductive container via the outer anode member, which is closer to the conductive container than to the transmissive target.

15. The X-ray generating apparatus according to claim 1, wherein the outer anode member and the transmissive target are hermetically joined in a ring pattern.

16. The X-ray generating apparatus according to claim 1, wherein the electron emitting source comprises a hot cathode.

17. The X-ray generating apparatus according to claim 1, wherein the electron emitting source is configured to irradiate the transmissive target with an electron beam.

18. The X-ray generating apparatus according to claim 1, wherein the transmissive target is configured to generate an X-ray in response to irradiation with an electron beam.

19. A radiography system comprising:

the X-ray generating apparatus of claim 1;

an X-ray detector configured to detect an X-ray that has been generated by the X-ray generating apparatus and transmitted through a subject; and a system control unit configured to control the X-ray generating apparatus and the X-ray detector in a coordinated manner.

* * * * *